(12) United States Patent
Pollock et al.

(10) Patent No.: US 12,295,788 B2
(45) Date of Patent: May 13, 2025

(54) GRIP APPARATUS FOR ULTRASOUND IMAGING TRANSDUCER DEVICE

(71) Applicants: Martin Joel Pollock, Winnipeg (CA); Bryan Clinton Kitchen, Winnipeg (CA)

(72) Inventors: Martin Joel Pollock, Winnipeg (CA); Bryan Clinton Kitchen, Winnipeg (CA)

(*) Notice: Subject to any disclaimer, the term of this patent is extended or adjusted under 35 U.S.C. 154(b) by 133 days.

(21) Appl. No.: 18/305,552

(22) Filed: Apr. 24, 2023

(65) Prior Publication Data

US 2023/0371925 A1 Nov. 23, 2023

Related U.S. Application Data

(60) Provisional application No. 63/343,770, filed on May 19, 2022.

(51) Int. Cl.
*A61B 8/00* (2006.01)

(52) U.S. Cl.
CPC .......... *A61B 8/4455* (2013.01); *A61B 8/4483* (2013.01)

(58) Field of Classification Search
CPC .............................. A61B 8/4455; A61B 8/4483
See application file for complete search history.

(56) References Cited

U.S. PATENT DOCUMENTS

| 5,752,517 | A | 5/1998 | Harman et al. |
| 8,118,747 | B2 | 2/2012 | Furia et al. |
| 2006/0173331 | A1 | 8/2006 | Booton et al. |
| 2018/0110497 | A1* | 4/2018 | Beacham ............... B33Y 80/00 |
| 2019/0076121 | A1* | 3/2019 | Southard .................. A61B 8/12 |

* cited by examiner

*Primary Examiner* — Joel F Brutus
(74) *Attorney, Agent, or Firm* — Ryan W. Dupuis; Michael R. Williams; Ade & Company Inc.

(57) ABSTRACT

A grip apparatus has a first body portion for gripping in a hand of an operator and a second body portion that releasably or integrally supports the acoustic window of an ultrasound imaging transducer. The first body portion has an upper surface parallel to the acoustic window at a location spaced upwardly from the acoustic window and a post extending upwardly from the upper surface to a radial enlargement such that the post is arranged to be gripped between two extended fingers of the hand of the operator below the radial enlargement while contacting the upper surface of the second body portion in a prone position of the hand. The post is spaced perpendicularly outward from the imaging plane of the acoustic window in a first direction. Two wing sections extend outwardly from opposing sides of the upper surface a second direction perpendicular to the first direction.

20 Claims, 7 Drawing Sheets

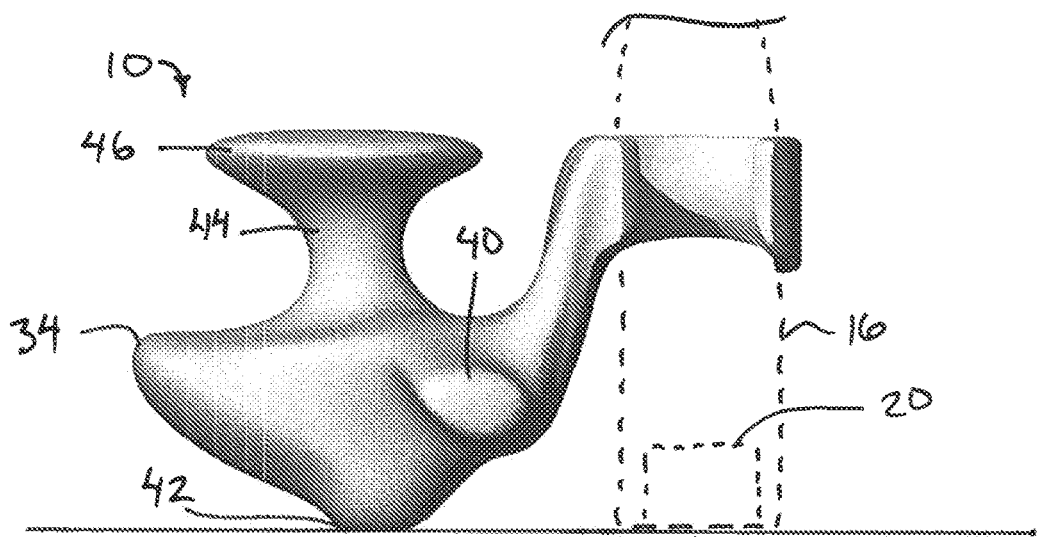
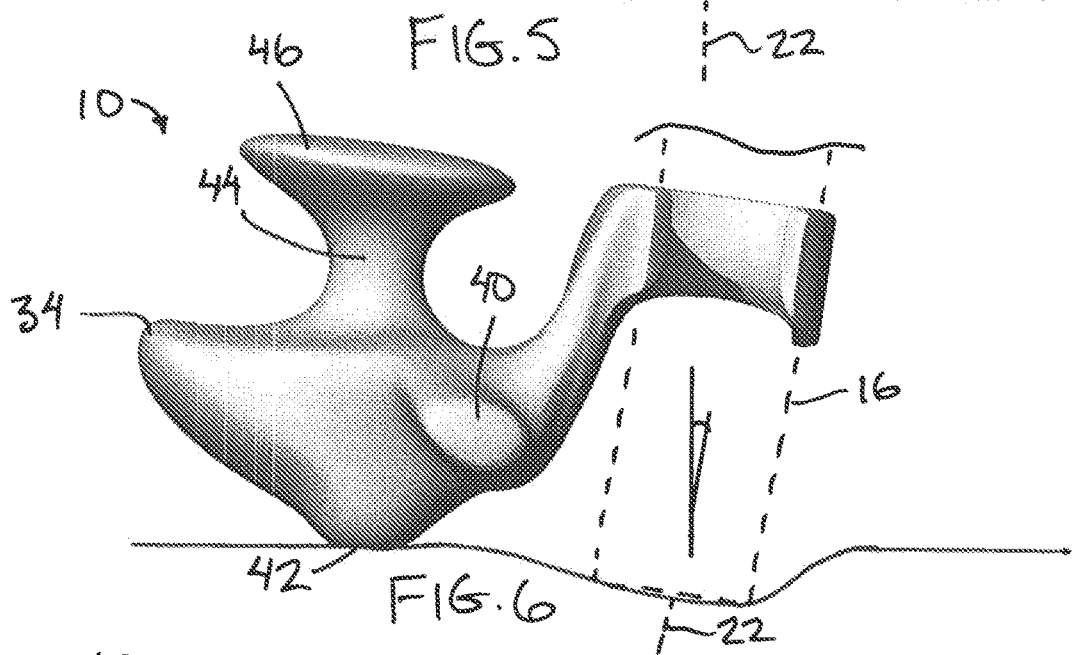
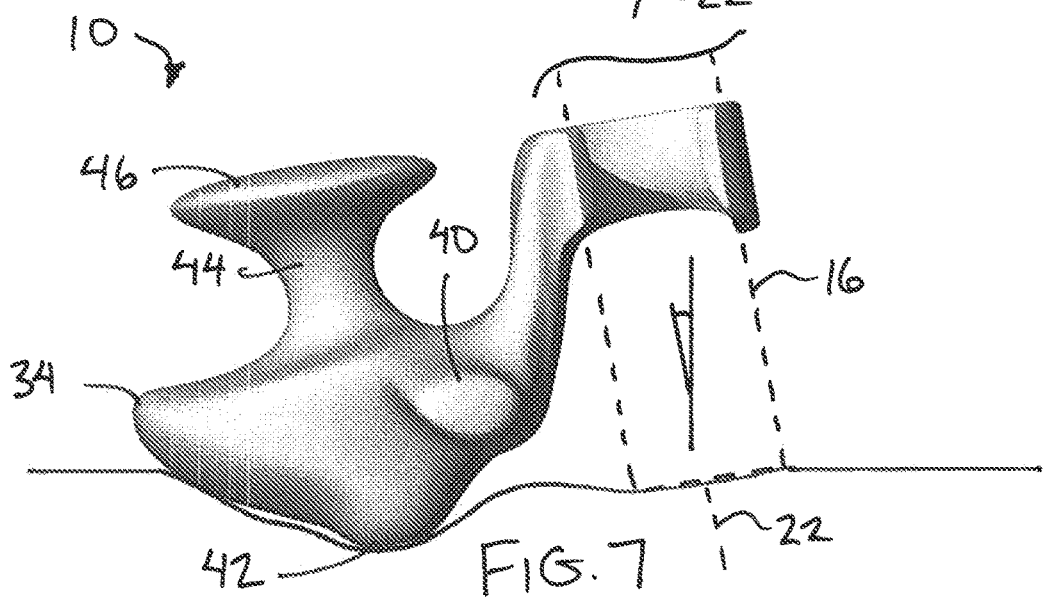

GRIP APPARATUS FOR ULTRASOUND IMAGING TRANSDUCER DEVICE

This application claims the benefit under 35 U.S.C. 119(e) of U.S. provisional application Ser. No. 63/343,770, filed May 19, 2022.

FIELD OF THE INVENTION

The present invention relates to a grip apparatus for use with the transducer device of an ultrasound imaging machine in which the transducer device includes a transducer array communicating through an acoustic window to scan an ultrasound image within an image plane of the transducer device. More particularly, the grip apparatus provides an ergonomic gripping structure arranged to be gripped in the hand of an operator of the ultrasound imaging machine, in which the grip apparatus may form part of an integral housing of the transducer device or may form an attachment that is releasably secured to a separate housing of the transducer device.

BACKGROUND

Ultrasound imaging machines are commonly used in a variety of diagnostic and medical procedures for obtaining images of internal structures of a subject, including human patients or animal patients. A typical ultrasound imaging machine includes a handheld transducer device comprising a probe housing arranged to be gripped in a hand of the operator and which has an array of transducer elements therein capable of communicating acoustic signals through an acoustic window forming a boundary portion of the probe housing that is intended to be in contact with the subject during an image scanning procedure. The acoustic window may be linear or curved, but in each instance is typically elongated in one direction so as to define an image plane aligned with the elongated direction of the acoustic window. Operators of ultrasound imaging machines must grip the transducer device in one hand and control the orientation of the image plane by flexing of the wrist. The repetitive motion and stability required by the wrist of the operator is known to be strenuous and can lead to various injuries to the operator.

U.S. Pat. No. 8,118,747 by Furia et al; U.S. Pat. No. 5,752,517 by Harman et al; and United States Patent Application Publication No. 2006/0173331 by Booton et al disclose a variety of ultrasound transducer housings which are intended to be ergonomic in shape; however, the devices disclosed provide limited opportunity to grip the housing in different orientations corresponding to different procedures being performed and/or generally rely on the strength of the wrist of the operator to provide stability in guiding the orientation of the image plane.

SUMMARY OF THE INVENTION

According to one aspect of the invention there is provided a grip apparatus for an ultrasound imaging transducer device, the ultrasound imaging transducer device including an acoustic window for contact with a subject and a transducer array for scanning an image plane through the acoustic window, the grip apparatus comprising:

a first body portion arranged to support the ultrasound imaging transducer device thereon;

a second body portion for gripping in a hand of an operator;

an upper surface on the second body portion positioned to lie generally parallel to at least a portion of the acoustic window at a location spaced upwardly from the acoustic window;

a post extending upwardly from the upper surface at a location spaced laterally outwardly from the acoustic window; and a radial enlargement on the post at a location spaced above the upper surface;

the post being sized so as to be arranged to be gripped between two extended fingers of the hand of the operator below the radial enlargement while contacting the upper surface of the second body portion in a prone position of the hand of the operator; and the post being shaped to be gripped between said two extended fingers in two different orientations angularly offset from one another about an upright axis of the post.

The arrangement of a post that can be gripped between extended fingers in a prone position of the hand in different angular orientations, together with the location of the post being offset in a lateral direction to one side of the acoustic window, maximizes the ability to suitably grip the transducer device in an ergonomic manner for a variety of different procedures.

In some embodiments, the ultrasound imaging transducer device comprises a probe housing which is elongated along a longitudinal axis oriented substantially perpendicularly to the acoustic window, and the first body portion is arranged to releasably mount the probe housing thereon. In this instance, the post is preferably spaced perpendicularly outwardly from the probe housing.

According to further embodiments, the first body portion may integrally house the acoustic window and the transducer array therein.

In either embodiment, the post is preferably spaced perpendicularly outwardly from the image plane of the transducer device.

Also in either embodiment, the upper surface of the second body portion may include a main section which is elongated in a first direction extending laterally away from the acoustic window towards a free end of the second body portion in which the post is located on the upper surface at an intermediate location partway between the acoustic window and the free end of the second body portion.

The upper surface of the second body portion preferably further includes two wing sections extending outwardly from opposing sides of the main section along a second direction oriented perpendicularly to the first direction of the main section. The wing sections preferably span an overall width in the second direction which is greater than a corresponding width of the acoustic window. Furthermore, the wing sections of the second body portion preferably have respective lower surfaces which are spaced above the acoustic window.

When the first body portion is arranged to releasably mount the probe housing thereon, the wing sections preferably span an overall width in the second direction which is greater than a corresponding width of the probe housing.

In either embodiment, the post is preferably shaped to be gripped between said two extended fingers in said two different orientations in which said two different orientations are at least 90 degrees apart from one another. More particularly, said two different orientations may be at least 120 degrees apart from one another.

Preferably the second body portion is symmetrical about a symmetry plane oriented perpendicularly to the image plane of the transducer array.

In some embodiments, the second body portion may further comprise a bottom surface below the upper surface in which the bottom surface is positioned to lie in a common plane with at least a portion of the acoustic window at a location spaced laterally outwardly from the acoustic window within said common plane so as to be arranged for contact with the subject during imaging.

When the bottom surface is spaced perpendicularly outwardly from the image plane of the transducer device in a first direction, a bottom side of the apparatus between the bottom surface and the acoustic window is preferably raised upwardly relative to said common plane.

The bottom surface may be spaced outwardly from the image plane by a distance which is greater than a width of the acoustic window measured within the image plane.

A contact area of the bottom surface may be equal to or less than a contact area of the acoustic window.

The bottom side of the second body portion may be tapered in the first direction towards the bottom surface and/or tapered towards the bottom surface in a second direction oriented perpendicularly to the first direction.

According to a further embodiment, the bottom side of the second body portion may be configured such that an entirety of the bottom surface is spaced upwardly from a plane of the acoustic window.

According to a second aspect of the invention there is provided a grip apparatus for an ultrasound imaging transducer device, the ultrasound imaging transducer device including an acoustic window for contact with a subject during imaging and a transducer array for scanning an image plane through the acoustic window, the grip apparatus comprising:
- a first body portion arranged to support the ultrasound imaging transducer device thereon;
- a second body portion for gripping in a hand of an operator;
- a bottom surface on the second body portion, the bottom surface being positioned to lie in a common plane with at least a portion of the acoustic window at a location spaced laterally outwardly from the acoustic window within said common plane so as to be arranged for contact with the subject during imaging;
- a post extending upwardly from an upper surface of the second body portion at a location above said bottom surface; and
- a radial enlargement on the post at a location spaced above the upper surface;
- the post being sized so as to be arranged to be gripped between two extended fingers of the hand of the operator below the radial enlargement while contacting the upper surface of the second body portion in a prone position of the hand of the operator.

The arrangement of a bottom surface which is spaced laterally outwardly from the acoustic window while remaining at least partly within a common plane with the acoustic window provides a second point of contact with the subject that acts as an outrigger relative to the contact of the acoustic window with the subject. This arrangement eases the requirement for the wrist of the operator to entirely stabilize the orientation of the image plane of the transducer device relative to the subject.

The bottom surface is preferably spaced outwardly from the image plane by a distance which is greater than a width of the acoustic window measured within the image plane.

Preferably, a contact area of the bottom surface is equal to or less than a contact area of the acoustic window.

Preferably a bottom side of the second body portion is tapered in the first direction towards the bottom surface and/or is tapered towards the bottom surface in a second direction oriented perpendicularly to the first direction.

BRIEF DESCRIPTION OF THE DRAWINGS

Various embodiments of the invention will now be described in conjunction with the accompanying drawings in which:

FIG. 5 is a schematic representation of the grip apparatus according to the first embodiment of FIG. 1 in a neutral position in which the image plane of the ultrasound imaging transducer device is substantially perpendicular to a surface of the object being scanned;

FIGS. 6 and 7 are schematic representations of the grip apparatus shown angularly deflected in two opposing directions from the neutral position of FIG. 5 respectively;

In the drawings like characters of reference indicate corresponding parts in the different figures.

DETAILED DESCRIPTION

Referring to the accompanying figures, there is illustrated a grip apparatus 10 for use with an ultrasound imaging machine 12.

Figure 11:
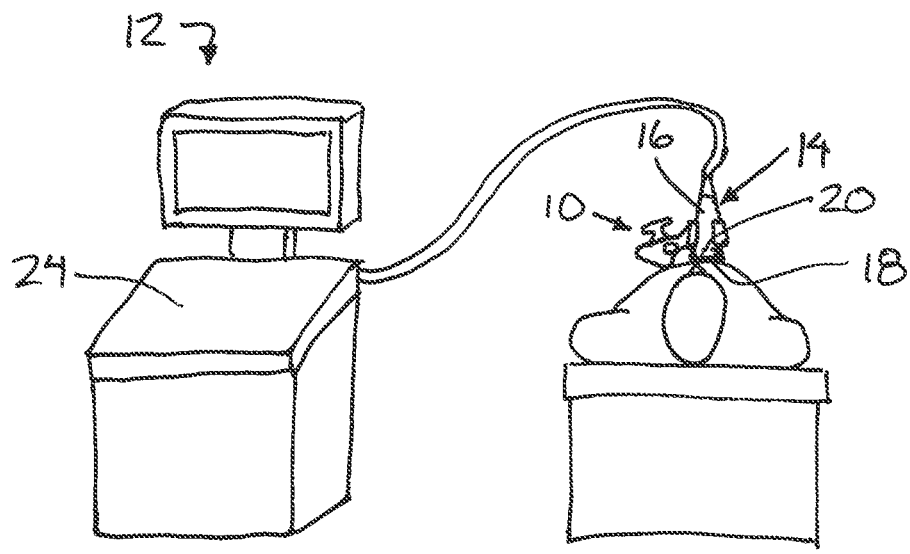
FIG. 11 is a schematic representation of the grip apparatus according to the first embodiment of FIG. 1, shown supported on an exemplary ultrasound imaging machine being used to scan an image of a subject.

As represented schematically in FIG. 11, the ultrasound imaging machine 12 typically comprises an ultrasound imaging transducer device 14 in the form of a probe arranged to be held in the hand of an operator for engagement with a subject, such as a human patient or an animal patient for scanning an image of the subject along an image plane extending into the subject. The ultrasound imaging transducer device 14 includes a probe housing 16 which includes an acoustic window 18 forming a lower boundary portion of the probe housing for contact with the subject. The acoustic window is configured such that ultrasonic signals can be transmitted therethrough when scanning and capturing an image. The probe housing is elongate in a direction of a longitudinal axis extending perpendicularly away from the acoustic window at the bottom end of the probe housing. The acoustic window 18 is typically elongate in a lateral direction that is perpendicular to the longitudinal axis of the housing. The acoustic window may be linear or curved across the width thereof in the lateral direction.

A transducer array 20 is supported within the probe housing 16 in proximity to the acoustic window such that the transducer array extends primarily in the lateral direction of the acoustic window. The transducer array 20 comprises a plurality of transducer elements which are arranged to transmit and receive ultrasonic signals for imaging purposes. The signals are communicated through the acoustic window so that the captured signals can be used to generate an image associated with the image plane 22 of the probe housing. The image plane 22 is occupied by both the lateral axis of the acoustic window and the longitudinal axis of the housing. In use, the acoustic window 18 is positioned against the surface of the subject such that the longitudinal axis of the probe housing extends generally perpendicularly outward from the surface in a neutral position according to FIG. 5. The probe housing can be tilted by the operator about a tilt axis oriented in the lateral direction of the transducer array such that the image plane can be tilted in either direction away from the neutral position of FIG. 5 into the tilted positions of FIG. 6 or FIG. 7.

The ultrasound machine 12 further includes a computer device 24 operatively connected with the transducer device 14 in which the computer device includes a memory storing program instructions thereon and a computer processor for executing the program instructions to perform the various functions of the ultrasound imaging machine. More particularly, the computer device 24 is arranged to direct the transducer device to generate ultrasound signals and capture reflected ultrasonic signals so that the captured signals can be processed into image data for generating an image representative of an image plane extending into the subject from the acoustic window of the transducer device.

In further embodiments, the computer device 24 may take the form of a portable tablet or smartphone that communicates with the transducer device so that the ultrasound signals can be either processed into images by the transducer device before communication to the computer device 24, or the ultrasound signals can be transmitted to the portable computer device for subsequent processing into images. In either instance, the images are displayed on the tablet or smartphone. The transducer device may communicate with the portable computer device by wired or wireless communication means.

Turning now to the grip apparatus 10, although various embodiments are shown in the accompanying figures, the features in common with the embodiments of FIGS. 1 to 13 will first be described herein.

In each instance, the grip apparatus 10 generally includes a unitary housing comprised of a first body portion 30 for operative connection to the ultrasound imaging transducer device 14 and a second body portion 32 which is shaped for gripping in the hand of the operator to control the position and orientation of the transducer device 14. The second body portion 32 extends primarily longitudinally in a first direction extending generally horizontally and perpendicularly outward from the first body portion 30 connected to the probe housing 16 at the front end of the apparatus towards a free end 34 at the rear end of the second body portion.

Figure 1:
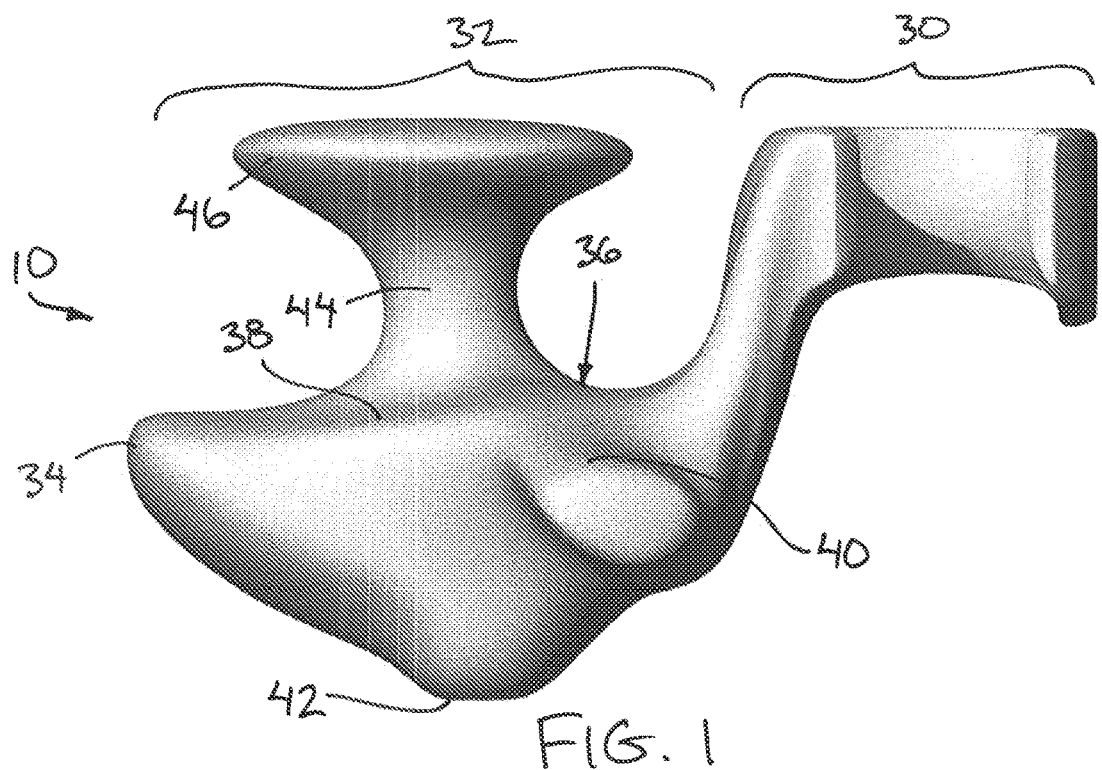
FIG. 1 is a side elevational view of a first embodiment of the grip apparatus which is arranged for releasable connection to an ultrasound imaging transducer device having a transducer array housed within a respective probe housing.
Figure 2:
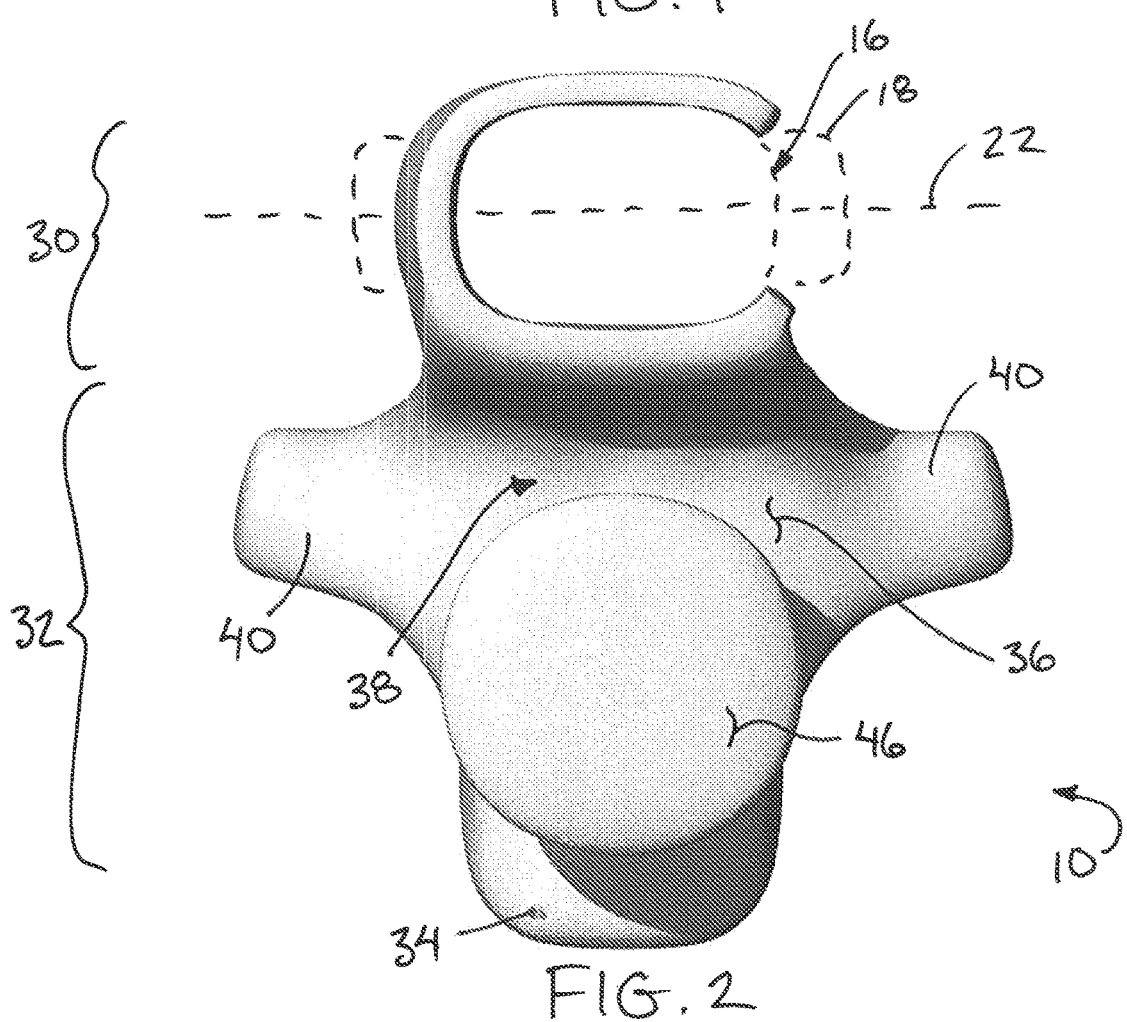
FIG. 2 is a top view of the grip apparatus according to the first embodiment of FIG. 1.
Figure 3:
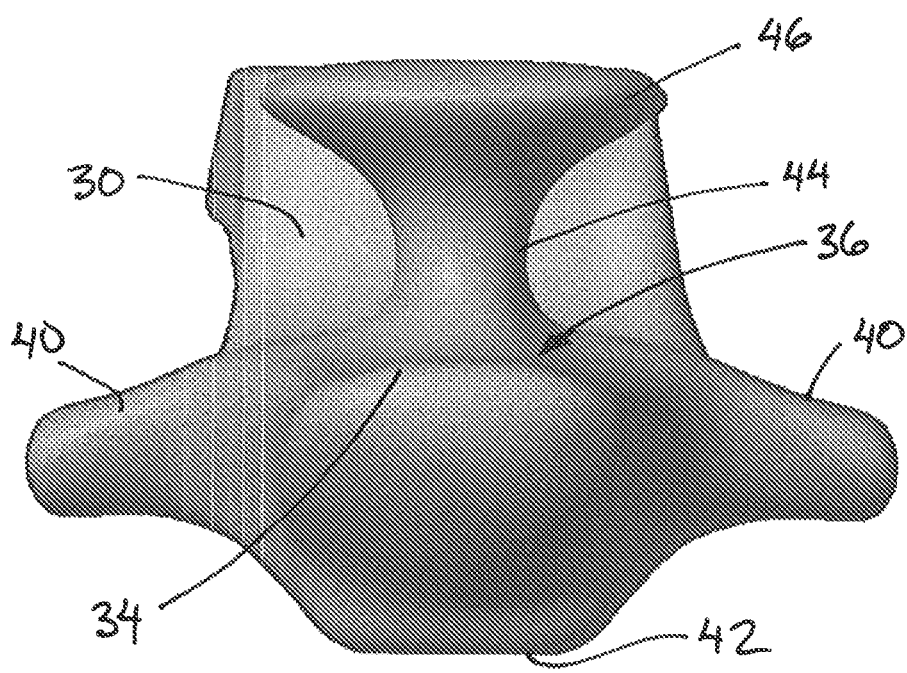
FIG. 3 is a rear elevational view of the grip apparatus according to the first embodiment of FIG. 1.
Figure 4:
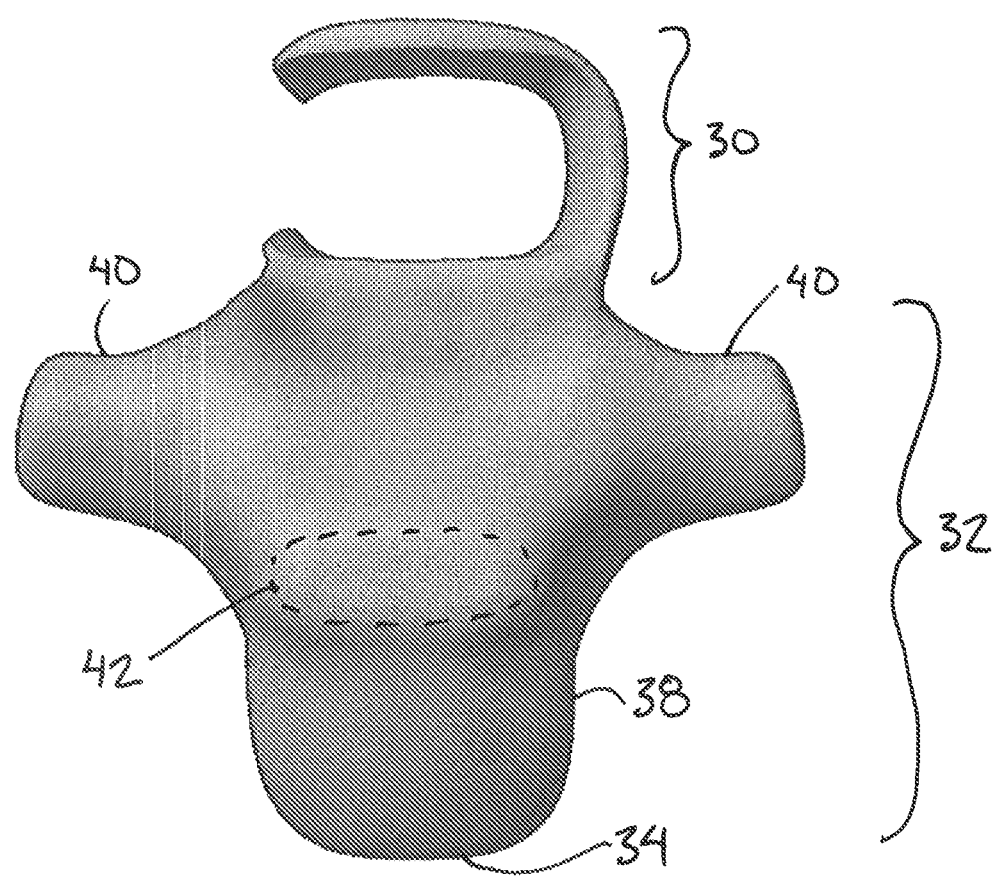
FIG. 4 is a bottom view of the grip apparatus according to the first embodiment of FIG. 1.
Figure 8:
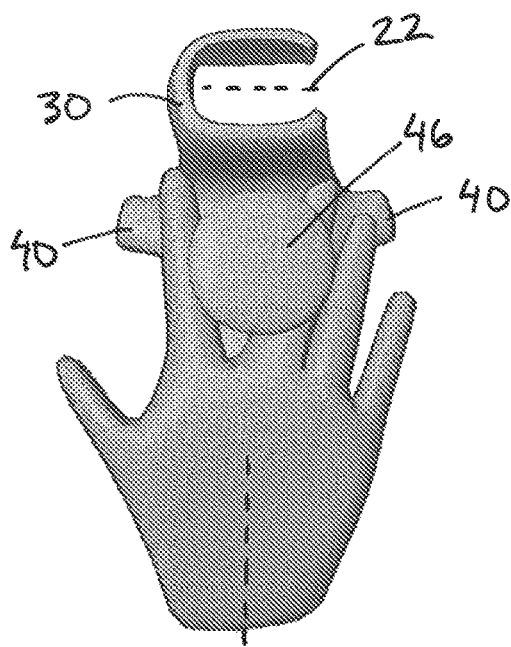
FIGS. 8, 9 and 10 are schematic representations of the grip apparatus according to the first embodiment of FIG. 1 shown gripped in a hand of the operator in different orientations that are angularly offset from one another about an upright axis of the apparatus.
Figure 9:
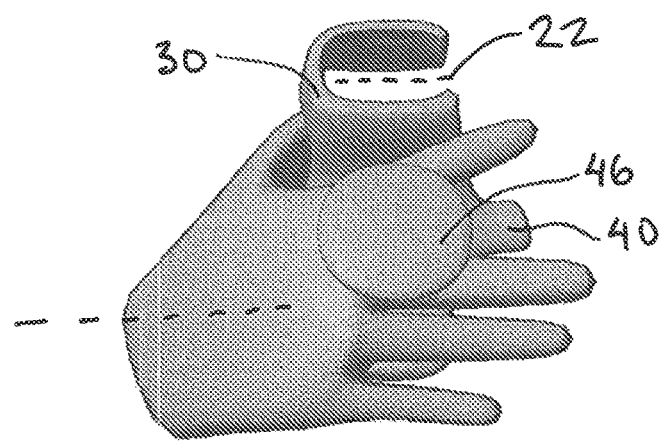
Figure 10:
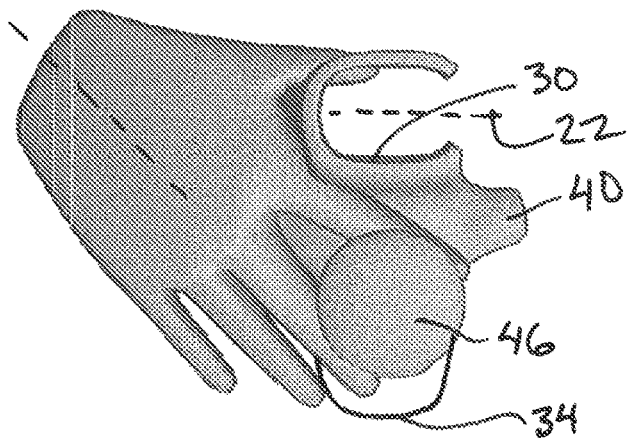

The second body portion 32 further includes an upper surface 36 arranged to be engaged by downward facing palm surfaces of a hand of the operator in a prone position during use as shown in each of the operating positions in FIGS. 8 to 10. A main section 38 of the upper surface is elongate in the first direction from the first body portion to the free end 34. The upper surface primarily lies in a plane which is parallel to the acoustic window of the transducer device while being spaced upwardly from the acoustic window of the transducer device.

The upper surface 36 further includes two wing sections 40 extending laterally outwardly from opposing sides of the main section 38 along a lateral axis oriented in a second direction which is perpendicular to said first direction noted above. The wing sections 40 of the second body portion have respective upper surfaces which are continuous with the main section of the upper surface 36 while each being sloped downwardly as the wing sections extend outwardly from the main section towards the ends of the wing sections which are lower in elevation than the upper surface of the main section 38. The wing sections are symmetrical about a symmetry plane oriented in the first direction while being perpendicular to the image plane and the acoustic window.

A bottom side of the second body portion is tapered downwardly and inwardly from opposing front and rear ends in the longitudinal or first direction to a bottom surface 42 of the second body portion. Likewise, the bottom sides of the wing sections are also tapered downwardly and inwardly in the lateral or second direction towards the bottom surface 42. The bottom surface 42 is thus centrally located in longitudinal and lateral directions of the second body portion while defining the lowermost surface of the apparatus 10. The bottom surface 42 has a surface area which is equal to or less than the surface area of the acoustic window for contact with the subject. The bottom surface 42 is generally elongate in the second direction and has rounded edges which smoothly transition into the inclined surfaces at the bottom side of the second body portion which form the longitudinally and laterally tapered shape of the bottom side of the apparatus 10.

The bottom surface 42 lies generally in a common plane with the acoustic window 18 of the probe housing 16 such that the bottom surface 42 of the second body portion and the acoustic window form two spaced apart contacts of the overall assembly of the transducer device 14 and grip apparatus 10 with the subject when in use. More particularly, the bottom surface 42 is spaced perpendicularly outward from the image plane of the probe housing so as to also be spaced outward in the first direction relative to the entirety of the probe housing 16 and the acoustic window therein. In the neutral position of FIG. 5, both the bottom surface 40 of the second body portion and the acoustic window of the probe housing 16 engage the surface of a subject at spaced apart positions when the image plane is oriented perpendicularly to the surface of the subject. A bottom side of the first body portion (and a front end of the second body portion) between the bottom surface 42 and the acoustic window 18 is raised upwardly from the acoustic window.

In this arrangement, the bottom surface 42 provides a second contact which adds stability so that the bottom surface 42 acts as an outrigger relative to the acoustic window 18 that forms primary contact of the transducer device with the subject. The small contact area of the bottom surface together with the tapered shape of the bottom side of the apparatus readily permits the bottom surface 42 to be pushed downwardly into soft tissues of a subject relative to the acoustic window when tilting the image plane in a first direction away from the neutral position as shown in FIG. 7. Likewise, the connection of the first body portion 30 of the apparatus to the probe housing 16 at a location spaced upwardly from the acoustic window does not interfere with the acoustic window at the bottom end of the probe housing to be similarly pushed downwardly into soft tissues of the subject relative to the bottom surface 40 when tilting the image plane in a second direction away from the neutral position as shown in FIG. 6. Tilting of the apparatus and connected probe housing 16 into either the first direction of FIG. 7 or the second direction of FIG. 6 can be accomplished with a downward pushing motion with the hand of the operator remaining in a prone position as described in further detail below.

The bottom side of the second body portion 32 below each wing section 40 is similarly raised upwardly from the bottom surface 42 and spaced upwardly from the acoustic window. The overall width of the grip apparatus in the second direction is defined by the overall width between opposing ends of the wing sections 40. The overall width defined by the wing sections 40 is greater than the probe housing and the acoustic window as measured in the second direction or as measured within the plane of the image plane. The overall width of the wing sections together with the bottom sides of the wing sections being raised upwardly further allow some degree of control by the operator to tilt the apparatus side to side using only downward force applied to either of the wing sections, thus further increasing the stability of the apparatus.

The apparatus 10 further includes a post 44 extending upwardly from the upper surface 36 of the second body portion. The post is generally circular in cross-section through a horizontal plane, while having a diameter which is sized to be comfortably fit and gripped between two extended fingers of the user. The post is centred in the lateral or second direction between the two wing sections 40. The post is also near the centre in the longitudinal or first direction of the second body portion between the first body portion 30 at the front end and the free end 34 at the rear end of the apparatus. In this manner the post 44 is spaced perpendicularly outwardly from each of the image plane, the acoustic window, the probe housing, and the first body portion that is operatively connected to the probe housing such that the bottom surface 42 is aligned with the upright axis of the post 44.

The apparatus 10 further includes a knob 46 supported at the top end of the post 44 at a location spaced above the wing sections in the form of a circular disk which is concentric with the post 44 but which has an outer diameter which is at least two times greater than a minimum outer diameter of the post. The knob 46 thus defines a radial enlargement which is enlarged in radial dimension relative to the remainder of the post 44 below. The top side of the radial enlargement of the knob 46 is flush with a flat top surface of the post 44 as shown in the Figures. The outer diameter of the post gradually increases from the minimum diameter at a central location along the height of the post towards both the top and bottom ends of the post such that the outer surface of the post gradually transitions into the underside of the radial enlargement 46 at the top end of the post and gradually transitions into the upper surface 36 of the second body portion at the bottom of the post. The overall height of the post is arranged to comfortably accommodate the thickness of the extended fingers of the operator in a prone position of the hand.

In use, the operator grips the post 44 between two extended fingers of a hand in the prone position such that the palm of the operator faces downward approximately parallel to the surface of the subject to be scanned and the acoustic window of the probe housing abutted against the surface of the subject. The operator can rotate their grip about the upright axis of the post between a plurality of different orientations which are angularly offset from one another about the post as shown in FIGS. 8 through 10 for example.

As shown in a first configuration in FIG. 8, the symmetrical shape of the body permits the apparatus to be comfortably gripped in either the left or right hand with the fingers extending forwardly in each instance such that a longitudinal axis of the hand or forearm of the user is oriented perpendicularly to the image plane of the probe housing. In this instance, the knuckles of the hand of the operator are approximately aligned with the free end 34 at the rear of the apparatus while the fingertips are positioned on the upper surface of the wing sections 40. This enables the apparatus to be tilted from the neutral position of FIG. 5 to either of the tilted orientations of FIG. 6 or FIG. 7 by transferring downward pressure between the fingertips on the wings and the knuckles on the free end 34 of the apparatus.

The right hand of the operator can be rotated in a first direction through a range of approximately 90 degrees from the neutral configuration of FIG. 8 to a first offset position shown in FIG. 9 in which the longitudinal axis of the hand and forearm of the user lies approximately parallel to the image plane of the probe housing. The opposing left-hand of the operator would be similarly rotated but in an opposing second direction through a range of 90 degrees from the neutral configuration of FIG. 8 to the first offset position for that hand. The hand of the operator is typically oriented so that the thumb of the hand is free to extend forwardly of the probe housing. In this position, downward pressure can be applied to the upper surface of the second body portion (i) at the front side between the wing sections 40 using the inside surface of the knuckle of the index finger and/or (ii) at the rear or free end 34 of the second body portion using the knuckle of the ring finger. Transferring downward pressure between these two locations again enables the apparatus to be tilted from the neutral position of FIG. 5 to either tilted orientations of FIG. 6 or FIG. 7.

Alternatively, the right hand of the operator can be rotated in the first direction from the neutral configuration of FIG. 8 through a range of more than 90 degrees to a second offset position shown in FIG. 10 in which the longitudinal axis of the hand and forearm of the user extends forwardly of the image plane of the probe housing. For example, the hand of the operator may be rotated to the second offset position through a range of 120°, 125°, 130°, 135°, 140°, 145°, or 150°. The opposing left hand of the operator would be similarly rotated but in an opposing second direction through the prescribed range of more than 90° from the neutral configuration of FIG. 8 to the second offset position for that hand. Again, in this instance the hand of the operator is oriented so that the thumb of the hand is free to extend forwardly of the probe housing. This can be useful for pulling the skin of the subject taught with the same hand that guides the probe housing 16 so that the other hand of the operator is free, for example to insert an intravenous needle into the subject in some instances. In the position of FIG. 10, downward pressure can be applied to the upper surface of the second body portion (i) at the front side between the wing sections 40 using the index finger and/or (ii) at the rear or free end 34 of the second body portion using the fingertips of the middle or ring fingers. Transferring downward pressure between these two locations again enables the apparatus to be tilted from the neutral position of FIG. 5 to either tilted orientations of FIG. 6 or FIG. 7. The location of the wing sections 40 longitudinally in the first direction between the post 44 and the acoustic window at the front end of the apparatus allows a downward facing palm surface of the hand of the operating to engage the upper surfaces of the wing sections 40 as shown in FIGS. 9 and 10.

Turning now more particularly to the first embodiment of FIGS. 1 through 11, in this instance, the probe housing 16 may be a conventional probe housing which is fully separate from the grip apparatus 10, in which the first body portion 30 of the grip apparatus 10 is arranged to be releasably clamped about the probe housing to fix the probe housing immovably relative to the grip apparatus 10. In the illustrated embodiment, the first body portion comprises a C-shaped channel extending about the longitudinal axis of the housing such that the channel is arranged to partly surround the probe housing and grip the housing therein. This may be accomplished by shaping and sizing the channel to extend about the probe housing in an interference fit which frictionally retains the probe housing relative to the grip apparatus. In further embodiments, the shape of the first body portion may vary or the configuration may vary to form a releasable attachment of the first body portion to other shapes and sizes of probe housings of various types of ultrasound imaging machines. In general, the first body portion extends upwardly above the upper surface of the second body portion so that even the bottom side of the first body portion remains spaced above the upper surface of the second body portion and well above the acoustic window so as not to interfere with the ability of the acoustic window of the probe housing to be pushed into the soft tissues of the subject when tilting the image plane as shown in FIG. 6.

Figure 12:
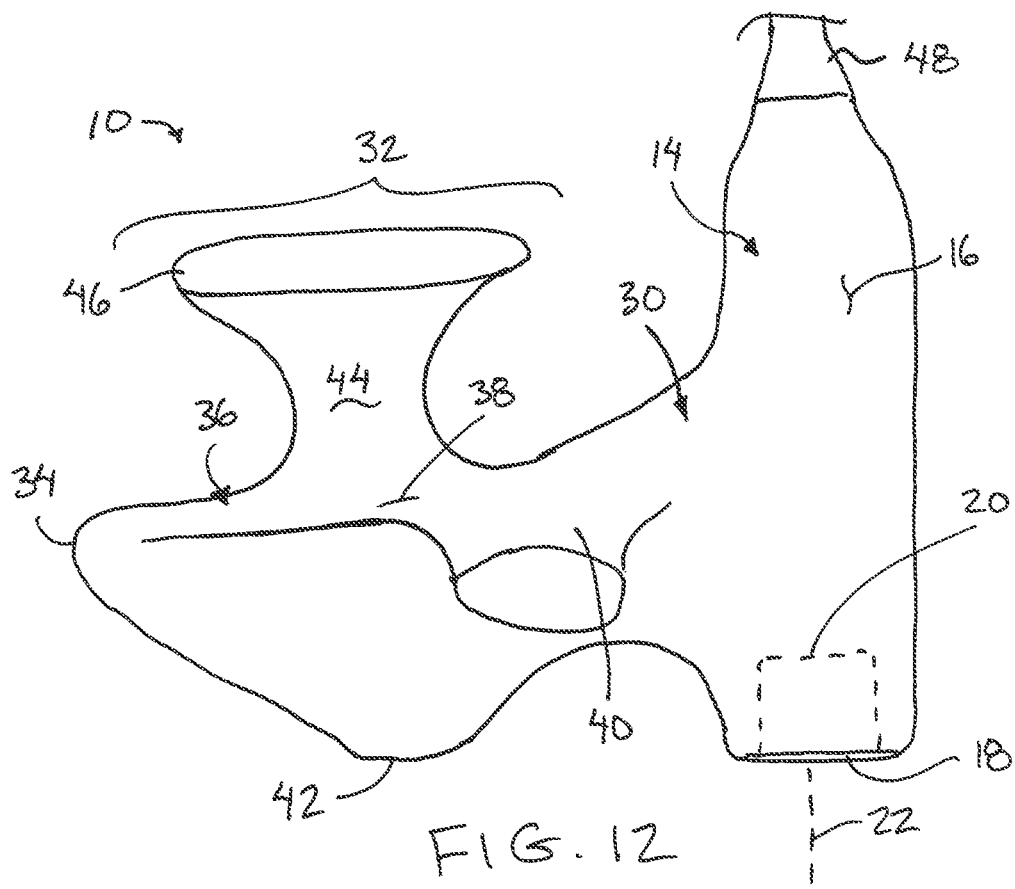
FIG. 12 is a side elevational view of a second embodiment of the grip apparatus which forms an integral probe housing of the ultrasound imaging transducer device so as to house the transducer array within the grip apparatus.

Turning now to a second embodiment of the grip apparatus 10 shown in FIG. 12, in this instance the first body portion 30 is formed to be continuous, seamless and unitary as a singular body with the structure of the probe housing 16. In this manner, the probe housing forms part of the first body portion so that the acoustic window forms a boundary portion of the first body portion of the apparatus and the transducer array 20 is housed within the first body portion for communicating signals through the acoustic window 18 as described above. The transducer array 20 may communicate externally to the associated computer device 24 of the machine 12 through a connected cable 48 as shown in FIG. 12 which exits through the top of the apparatus 10 at the front end thereof.

Figure 13:
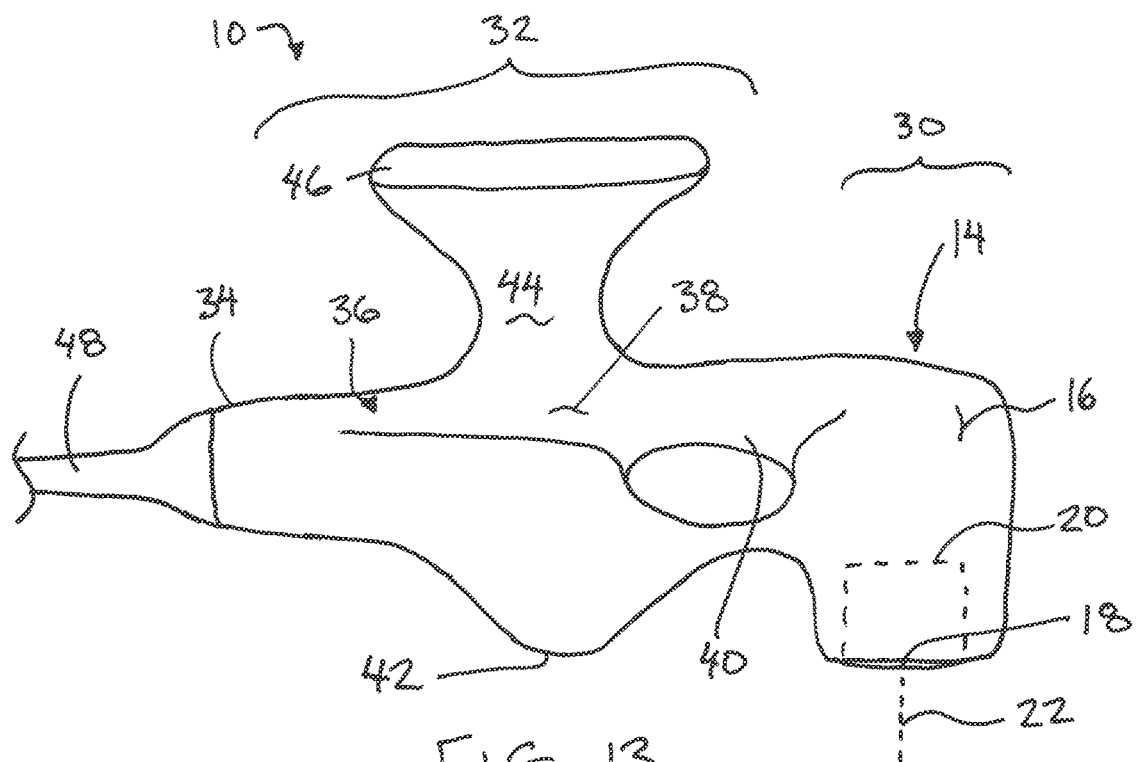
FIG. 13 is a side elevational view of a third embodiment of the grip apparatus which forms an integral probe housing of the ultrasound imaging transducer device so as to house the transducer array within the grip apparatus.

According to a third embodiment of the grip apparatus 10 shown in FIG. 13, in which the first body portion 30 is again formed to be continuous, seamless, and unitary as a singular body with the structure of the probe housing 16. In this manner, the probe housing forms part of the first body portion so that the acoustic window forms a boundary portion of the first body portion of the apparatus and the transducer array 20 is housed within the first body portion for communicating signals through the acoustic window 18 as described above. The transducer array 20 may communicate externally to the associated computer device 24 of the machine 12 through a connected cable 48 as shown in FIG. 13 which exits from the free end 34 of the second body portion at the rear of the apparatus.

According to a further embodiment (not shown) the grip apparatus is configured identically to the embodiments of FIGS. 12 and 13, but with the cable 48 removed. The transducer array 20 within the first body portion in this instance communicates with the processor of the computer device 24 through a transceiver module providing wireless communication for subsequent processing of the signals to generate images by the computer device 24.

Figure 14:
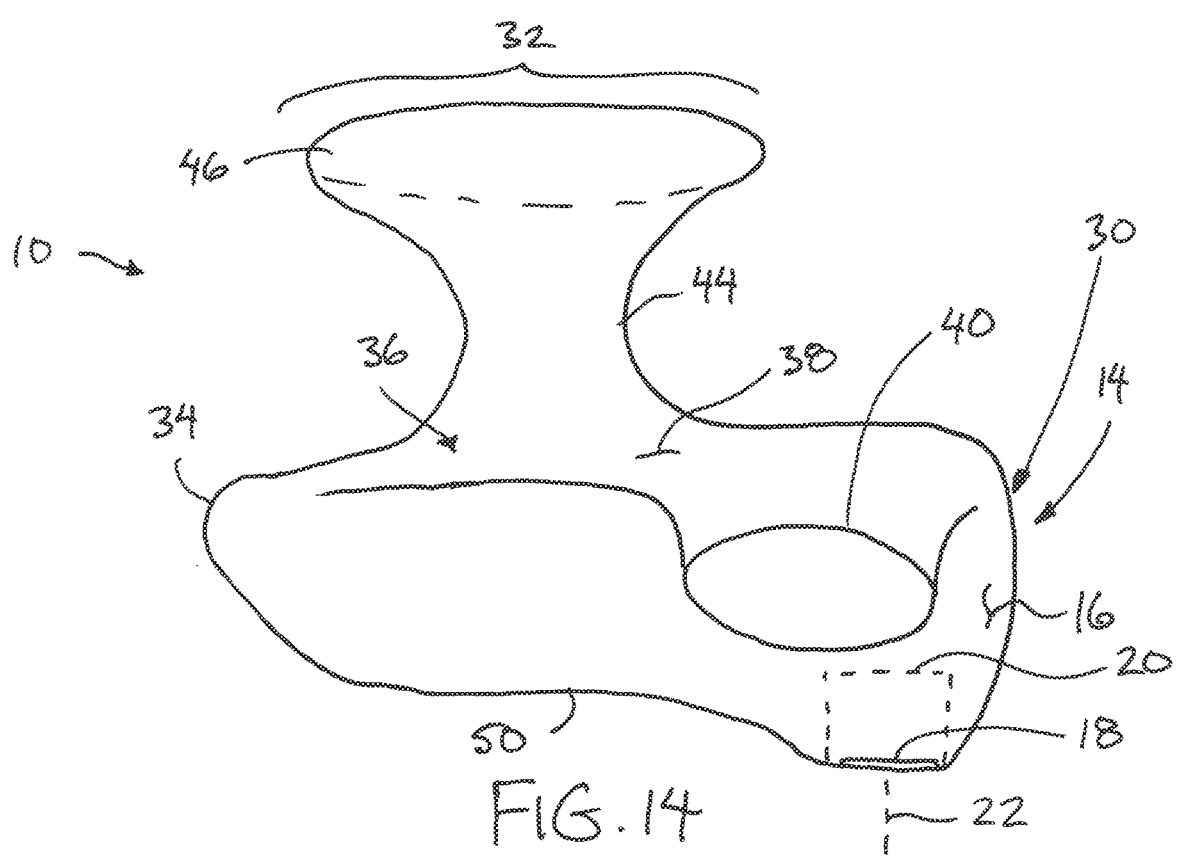
FIG. 14 is a side elevational view of a fourth embodiment of the grip apparatus which forms an integral probe housing of the ultrasound imaging transducer device so as to house the transducer array within the grip apparatus.
Figure 15:
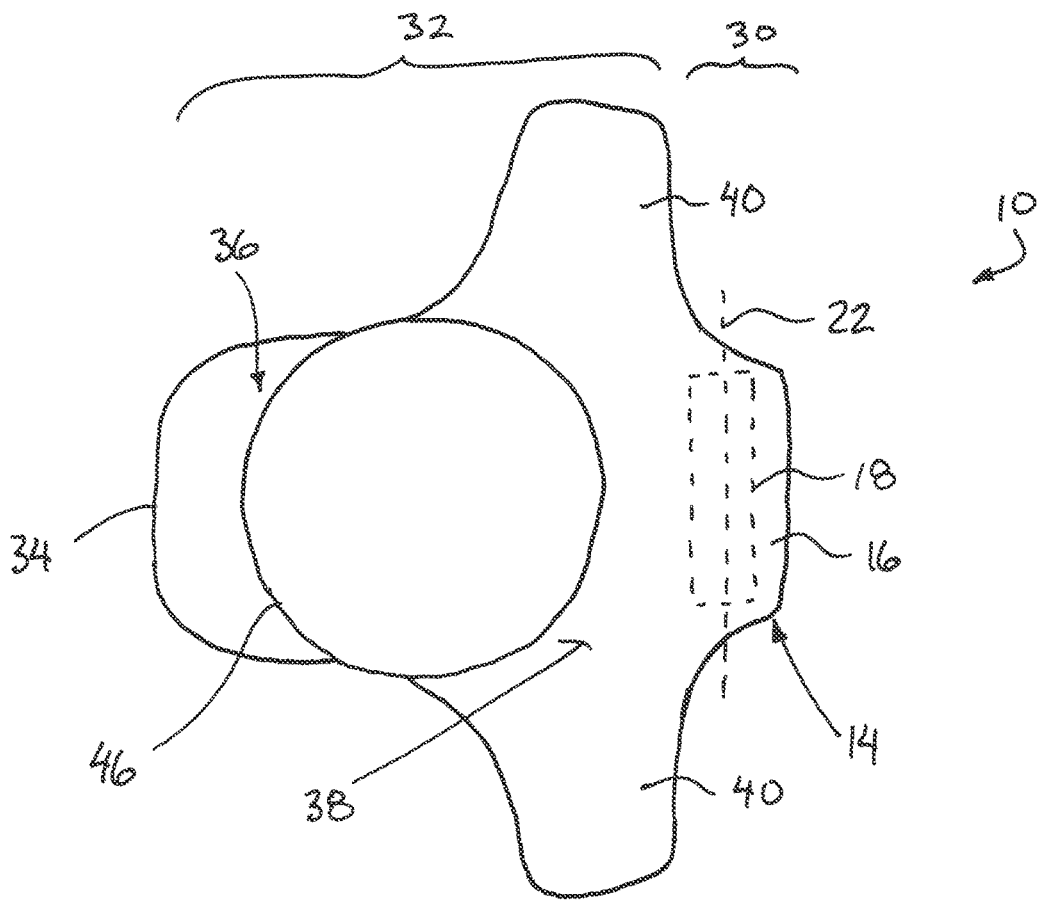
FIG. 15 is a top view of the grip apparatus according to the fourth embodiment of FIG. 14.
Figure 16:
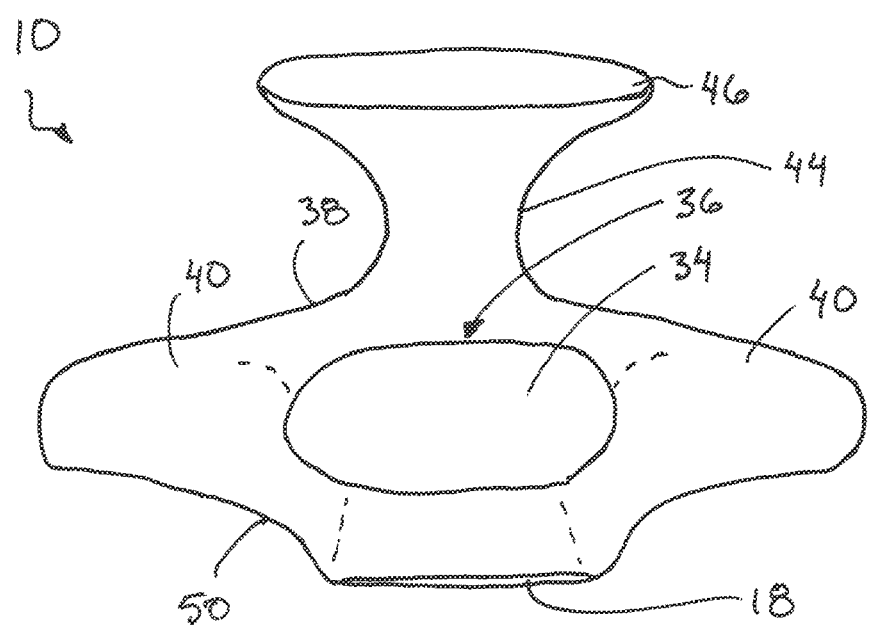
FIG. 16 is a rear elevational view of the grip apparatus according to the fourth embodiment of FIG. 14.

Turning now to FIGS. 14 through 16, according to a further embodiment of the grip apparatus 10, the grip apparatus again comprises a unitary housing including (i) a first body portion 30 integrally supporting components of the ultrasound imaging transducer 14 including the transducer array 20 and the acoustic window 18 which generates an image within an imaging plane 22 of the transducer, and (ii) a second body portion which is shaped for gripping in the hand of the operator to control the position and orientation of the imaging plane 22 of the transducer device 14. The second body portion 32 extends primarily longitudinally in a first direction extending generally horizontally and perpendicularly rearward from the imaging plane 22 of the array 20 on the first body portion 30 towards the rear end 34 of the second body portion. In this instance, the components of the transducer device communicate wirelessly with the computer 24 such that there is no need for a cord 48 to connect the apparatus to the computer according to some previous embodiments.

The second body portion in this instance is substantially identical to the previous embodiments with regard to (i) the general shape of the upper surface 36 of the second body portion having a main section extending longitudinally to the rear end 34, (ii) the wing sections 40 which have respective upper surfaces which are continuous with the main section of the upper surface 36, (iii) the post 44 extending upwardly from the upper surface 36 at a location spaced perpendicularly rearward from the image plane 22, and (iv) the radial enlargement of the knob 46 to receive extended fingers of the user between the upper surface 36 and the knob 46 in the manner described above.

The embodiment of FIGS. 14 to 16 differs primarily from the previous embodiments by the absence of a bottom surface 42 in a common plane with the acoustic window 18. In this instance, the entire bottom side 50 of the apparatus tapers in a first longitudinal direction towards the acoustic window 18 so as to be sloped primarily downwardly and forwardly from the rear end 34 to the acoustic window 18 as best shown in FIG. 14. In addition, the bottom surfaces 50 at the wing sections 44 are tapered in a second lateral direction towards the acoustic window 18 such that the underside of each wing section 40 is sloped downwardly and laterally inwardly from the distal end of the wing section to the acoustic window 18 as best shown in FIG. 16. When the acoustic window is oriented in a horizontal orientation, the acoustic window forms the lowermost portion of the apparatus 10 and the entire bottom surface 50 of the grip apparatus is sloped upwardly and away from the acoustic window in all directions.

In this manner, an entirety of the bottom surface 50 of the apparatus is spaced upwardly from the plane of the acoustic window to maximize the ability to change the angular orientation of the imaging plane relative to the subject upon which the ultrasound procedure is being performed. Due in part to the wireless communication of the transducer device 14 with the computer 24 such that no cord 48 is required, and due in part to the compact and balanced configuration of the first and second body portions 30 and 32 of the apparatus 10, the user can grip the apparatus of the embodiment of FIGS. 14 to 16 using the hand positioning according to FIGS. 8 through 10 in a stable manner without any considerable strain on the wrist such that the additional support provided by the bottom surface 42 in the previous embodiments is not required in this instance.

In further embodiments, an ultraviolet (UV) light source may be further incorporated into the unitary housing of the apparatus 10 to project UV light downwardly in the direction that the acoustic window faces for purposes of illuminating veins of the subject below the surface of the skin, for example when using ultrasound to locate veins for placement of an intravenous needle.

In further embodiments, the post 44 may comprise a collapsible structure or an adjustable structure which can be adjusted in overall height to vary how the apparatus is gripped or to accommodate different user preferences. In the instance of a collapsible post, the boundary of the post may be formed of a stacked series of annular segments of gradually increasing outer diameter which can be folded into a nested arrangement relative to one another to collapse the overall height of the post.

In further embodiments, one or more activation buttons may be incorporated into the grip apparatus, in alignment with finger placement according to one or more gripping orientations of the grip apparatus. In this instance, the activation buttons may be linked to various functions of the ultrasound imaging machine, for example commanding the machine to capture and record a still image or a video clip among the ultrasound images being captured and displayed by the machine.

Since various modifications can be made in the invention as herein above described, and many apparently widely different embodiments of same made, it is intended that all matter contained in the accompanying specification shall be interpreted as illustrative only and not in a limiting sense.

The invention claimed is:

1. A grip apparatus for an ultrasound imaging transducer device, the ultrasound imaging transducer device including an acoustic window for contact with a subject and a transducer array for scanning an image plane through the acoustic window, the grip apparatus comprising:
   a first body portion arranged to support the ultrasound imaging transducer device thereon at a front and a bottom of the apparatus;
   a second body portion for gripping in a hand of an operator, the second body portion extending longitudinally rearward in a first direction from the first body portion to a free end of the second body portion at a rear of the apparatus opposite from the acoustic window at the front of the apparatus;
   an upper surface on the second body portion extending in the first direction between the first body portion and the free end of the second body portion such that the upper surface is positioned to lie generally parallel to at least a portion of the acoustic window at a location spaced upwardly from the acoustic window;
   a post extending upwardly along an upright axis from the upper surface on the second body portion, the post being spaced from the acoustic window in the first direction so as to extend upwardly from the upper surface partway between the acoustic window at the front of the apparatus and the free end at the rear of the apparatus; and
   a radial enlargement on the post at a location spaced above the upper surface;
   the post being sized so as to be arranged to be gripped between two extended fingers of the hand of the operator in a prone position of the hand such that the extended fingers are received below the radial enlargement while contacting the upper surface of the second body portion;
   the post being shaped to be gripped between said two extended fingers in two different orientations angularly offset from one another about said upright axis of the post in which said two different orientations are at least 90 degrees apart from one another; and
   the upper surface being configured to be engaged by a downward facing palm surface of said hand of the operator while the post is gripped between said two extended fingers of said hand of the operator in the prone position in each of said different orientations.

2. The grip apparatus according to claim 1 wherein the ultrasound imaging transducer device comprises a probe housing which is elongated along a longitudinal axis oriented substantially perpendicularly to the acoustic window, and wherein the first body portion is arranged to releasably mount the probe housing thereon.

3. The grip apparatus according to claim 1 wherein the first body portion integrally houses the acoustic window and the transducer array therein.

4. The grip apparatus according to claim 1 wherein the the first direction extends perpendicularly outwardly from the image plane of the transducer device.

5. The grip apparatus according to claim 4 wherein the ultrasound imaging transducer device comprises a probe housing which is elongated along a longitudinal axis oriented substantially perpendicularly to the acoustic window, wherein the first body portion is arranged to releasably mount the probe housing thereon, and wherein the post is spaced perpendicularly outwardly from the probe housing.

6. The grip apparatus according to claim 1 wherein the upper surface of the second body portion includes a main section which is elongated in said first direction and two wing sections extending outwardly from opposing sides of the main section along a second direction oriented perpendicularly to the first direction of the main section.

7. The grip apparatus according to claim 1 wherein said two different orientations are at least 120 degrees apart from one another.

8. The grip apparatus according to claim 1 wherein the second body portion further comprises a bottom surface below the upper surface, the bottom surface being positioned to lie in a common plane with at least a portion of the acoustic window at a location spaced in the first direction from the acoustic window within said common plane so as to be arranged for contact with the subject during imaging.

9. The grip apparatus according to claim 1 wherein the second body portion further comprises a bottom surface below the upper surface, the bottom surface being configured such that an entirety of the bottom surface is spaced upwardly from a plane of the acoustic window.

10. The grip apparatus according to claim 1 wherein the post has a flat top surface and wherein a top side of the radial enlargement is flush with the flat top surface of the post.

11. A grip apparatus for an ultrasound imaging transducer device, the ultrasound imaging transducer device including an acoustic window for contact with a subject during imaging and a transducer array for scanning an image plane through the acoustic window, the grip apparatus comprising:
   a first body portion arranged to support the ultrasound imaging transducer device thereon at a front and a bottom of the apparatus;
   a second body portion for gripping in a hand of an operator, the second body portion extending longitudinally rearward in a first direction from the first body portion to a free end of the second body portion at a rear of the apparatus opposite from the acoustic window at the front of the apparatus;

an upper surface on the second body portion extending in the first direction between the first body portion and the free end of the second body portion such that the upper surface is positioned to lie generally parallel to at least a portion of the acoustic window at a location spaced upwardly from the acoustic window;

a post extending upwardly along an upright axis from the upper surface of the second body portion, the post being spaced from the acoustic window in the first direction so as to extend upwardly from the upper surface at an intermediate location partway between the acoustic window at the front of the apparatus and the free end at the rear of the apparatus;

a radial enlargement on the post at a location spaced above the upper surface;

the post being sized so as to be arranged to be gripped between two extended fingers of the hand of the operator in a prone position of the hand such that the extended fingers are received below the radial enlargement while contacting the upper surface of the second body portion;

the upper surface being configured to be engaged by a downward facing palm surface of said hand of the operator while the post is gripped between said two extended fingers of said hand of the operator in the prone position in each of a plurality of different orientations; and a bottom surface on the second body portion arranged for contact with the subject during imaging;

wherein the bottom surface is positioned to lie in a common plane with at least a portion of the acoustic window at a location spaced from the acoustic window in the first direction; and wherein the bottom surface is in alignment with the upright axis of the post.

12. The grip apparatus according to claim 11 wherein a contact area of the bottom surface is equal to or less than a contact area of the acoustic window.

13. The grip apparatus according to claim 11 wherein a bottom side of the second body portion is tapered downwardly and inwardly from both the front and the rear in the first direction towards the bottom surface and wherein said bottom side of the second body portion is further tapered in a second direction from laterally opposing sides towards the bottom surface in which the second direction is oriented perpendicularly to the first direction.

14. A grip apparatus for an ultrasound imaging transducer device, the ultrasound imaging transducer device including an acoustic window for contact with a subject during imaging and a transducer array for scanning an image plane through the acoustic window, the grip apparatus comprising:

a first body portion arranged to support the ultrasound imaging transducer device thereon at a front and a bottom of the apparatus;

a second body portion for gripping in a hand of an operator, the second body portion including (i) a main section extending longitudinally rearward in a first direction from the first body portion to a free end of the second body portion at a rear of the apparatus opposite from the acoustic window at the front of the apparatus and (ii) two wing sections protruding laterally outwardly from opposing sides of the main section in a second direction oriented perpendicularly to the first direction;

an upper surface of the main section of the second body portion extending in the first direction between the first body portion and the free end of the second body portion such that the upper surface of the main section is positioned to lie generally parallel to at least a portion of the acoustic window at a location spaced upwardly from the acoustic window;

a post extending upwardly along an upright axis from the upper surface of the main section of the second body portion, the post being spaced from the acoustic window in the first direction so as to extend upwardly from the second body portion at an intermediate location partway between the acoustic window at the front of the apparatus and the free end at the rear of the apparatus;

a radial enlargement on the post at a location spaced above the second body portion;

the post being sized so as to be arranged to be gripped between two extended fingers of the hand of the operator in a prone position of the hand such that the extended fingers are received below the radial enlargement while contacting the upper surface of the second body portion;

the upper surfaces of the wing sections being configured to be engaged by fingertips of said hand of the operator while the post is gripped between said two extended fingers of said hand of the operator in the prone position.

15. The grip apparatus according to claim 14 wherein the wing sections span an overall width in the second direction which is greater than a corresponding width of the acoustic window.

16. The grip apparatus according to claim 14 wherein the ultrasound imaging transducer device comprises a probe housing which is elongated along a longitudinal axis oriented substantially perpendicularly to the acoustic window, wherein the first body portion is arranged to releasably mount the probe housing thereon, and wherein the wing sections span an overall width in the second direction which is greater than a corresponding width of the probe housing.

17. The grip apparatus according to claim 14 wherein the second direction is parallel to the image plane of the transducer array.

18. The grip apparatus according to claim 14 wherein each wing section has an upper surface extending continuously from the upper surface of the main section of the second body portion.

19. The grip apparatus according to claim 14 wherein the wing sections are situated between the acoustic window and the post in the first direction.

20. The grip apparatus according to claim 14 wherein the upper surface of each wing section is configured to be engaged by a downward facing palm surface of said hand of the operator while the post is gripped between said two extended fingers of said hand of the operator in the prone position.

* * * * *